(12) United States Patent
Spahn

(10) Patent No.: US 7,851,736 B2
(45) Date of Patent: Dec. 14, 2010

(54) METHOD AND DEVICE FOR OPTIMIZING THE IMAGE DISPLAY ON IMAGING APPARATUSES OF A MEDICAL SYSTEM DURING A MEDICAL PROCEDURE

(75) Inventor: Martin Spahn, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 827 days.

(21) Appl. No.: 11/715,536

(22) Filed: Mar. 8, 2007

(65) Prior Publication Data
US 2007/0230666 A1 Oct. 4, 2007

(30) Foreign Application Priority Data
Mar. 10, 2006 (DE) .............. 10 2006 011 233

(51) Int. Cl.
*G01J 1/32* (2006.01)
(52) U.S. Cl. ............ 250/205; 250/208.1; 378/65; 378/114; 378/117
(58) Field of Classification Search ............ 250/208.1, 250/205; 348/222.1, 78, 50, 207, 68, 73; 351/237; 382/260; 345/10, 11; 378/64, 378/65, 114–117, 145, 190, 210
See application file for complete search history.

(56) References Cited

U.S. PATENT DOCUMENTS

| 4,973,149 | A | 11/1990 | Hutchinson |
| 5,091,926 | A * | 2/1992 | Horton et al. ............ 378/114 |
| 6,033,072 | A | 3/2000 | Ono et al. |
| 6,401,050 | B1 | 6/2002 | Cooke et al. |
| 6,483,485 | B1 * | 11/2002 | Huang et al. ............ 345/10 |
| 2004/0034534 | A1 | 2/2004 | Sander et al. |
| 2005/0132408 | A1 * | 6/2005 | Dahley et al. ............ 725/80 |
| 2005/0206583 | A1 | 9/2005 | Lemelson et al. |

FOREIGN PATENT DOCUMENTS

| DE | 10226539 A1 | 1/2004 |
| WO | 04052225 A2 | 6/2004 |
| WO | WO 2006087689 A2 * | 8/2006 |

* cited by examiner

*Primary Examiner*—Thanh X Luu
*Assistant Examiner*—Francis M Legasse, Jr.

(57) ABSTRACT

A method and a device for optimizing the image display on imaging apparatuses register whether an operator is looking at the imaging apparatus. The image display of the imaging apparatus is optimized, when it is registered that the operator is looking at the imaging apparatus and namely by dimming the room lighting and/or by increasing the contrast of the imaging apparatus.

18 Claims, 1 Drawing Sheet

METHOD AND DEVICE FOR OPTIMIZING THE IMAGE DISPLAY ON IMAGING APPARATUSES OF A MEDICAL SYSTEM DURING A MEDICAL PROCEDURE

CROSS REFERENCE TO RELATED APPLICATIONS

This application claims priority of German application No. 10 2006 011 233.4 filed Mar. 10, 2006, which is incorporated by reference herein in its entirety.

FIELD OF THE INVENTION

The present invention relates to a method and a device for optimizing the image display on imaging apparatuses. The method and the device are particularly suited to use in diagnostic or interventional operations.

BACKGROUND OF THE INVENTION

During a diagnostic or interventional operation, the relevant operation site is recorded by a camera and displayed on a monitor. The monitors in a cardiological or angiographical suite (x-ray method) are usually attached above the table, upon which the patient lies, opposite the cardiologist or radiologist. The monitors are suspended from the ceiling of the operating room for instance.

During the diagnostic or interventional operation, the operating room must be brightly illuminated so that the physician has an optimum view of the patient during the operation and also during preparatory activities, such as preparing a new catheter for instance. However, the bright lighting of the room impairs the perceptibility on the monitor.

An optimum image quality during diagnostic imaging methods is influenced by a wide variety of components and/or parameters. Among these components and/or parameters are the registration and sensor technology (e.g. flat panel detector based on cesium iodide and amorphous silicon during cardiology or angiography x-rays), the image processing and also image observation. While a great deal of know-how is invested in the sensor technology and image processing, the image display on the monitor is frequently neglected.

SUMMARY OF THE INVENTION

The object of the present invention is to provide a method and a device for optimizing the image display on imaging apparatuses, which optimize the image display on the imaging apparatus in a suitable manner.

This object is achieved by the method and the device having the features of the independent claims. Advantageous developments are defined in the subclaims.

With the method according to the invention for optimizing the image display on imaging apparatuses, a gradual dimming of the room lighting is preferably advantageously achieved according to a first variant in that the operator and/or the eye of the operator is registered/monitored by means of a camera in order to determine whether or not the operator is looking at the imaging apparatus. In particular, the operator's eye movements and thus his/her gaze into the camera can be detected. As soon as the operator views the monitor during a diagnostic or interventional examination, the room lighting is preferably dimmed slightly. Said dimming indirectly improves the contrast on the monitor. An eye and/or pupil detection software is preferably able to detect at any time whether the operator is looking at the monitor. The room lighting and/or the light which particularly influences the contrast of the monitor is dimmed by means of this information for instance.

Advantageously the operating room is not constantly illuminated brightly during the diagnostic or interventional operation, but rather as a function of whether the operator is observing the monitor, e.g. while x-raying, or is on the other hand occupied with other activities such as preparing a new catheter for instance.

The image quality improves by dimming the room lighting, i.e. it increases the perceptive contrast on the monitor (or monitors), while the operator observes the monitor. By dimming the room lighting, the eye of the operator adapts and the observed contrast on the monitor appears increased.

According to a second variant, the contrast of the imaging apparatus can also be directly increased to optimize the image display, if the operator is looking at the imaging apparatus. The stronger contrast advantageously significantly increases the perceptibility on the monitor. This occurs by reducing the so-called window (or contrast). The advantage of this method lies in the improvement in the perceptibility of objects on the monitor image and thus an improvement in the image quality. In general, this positively influences the diagnosis and intervention.

Alternatively to the camera registering the eye, a photo sensor registers whether the operator is looking at the imaging apparatus. In this way, a light source can be attached to the head of the operator, said light source preferably emitting a wedge-shaped infrared light beam and a light receiver can be arranged in the vicinity of the imaging apparatus. As soon as the light receiver receives the light beam, it sends a signal to a control device, which then triggers the optimization of the image display.

The imaging apparatus is preferably a monitor or a video projector. The video projector is advantageous in that the display is represented on a large screen, the position of which can be changed in a simple fashion.

BRIEF DESCRIPTION OF THE DRAWINGS

Preferred embodiments of the invention are described from now on with reference to the appended drawings, in which.

DETAILED DESCRIPTION OF THE INVENTION

The exemplary embodiments of the present invention are described below with reference to the drawings.

Figure 1:
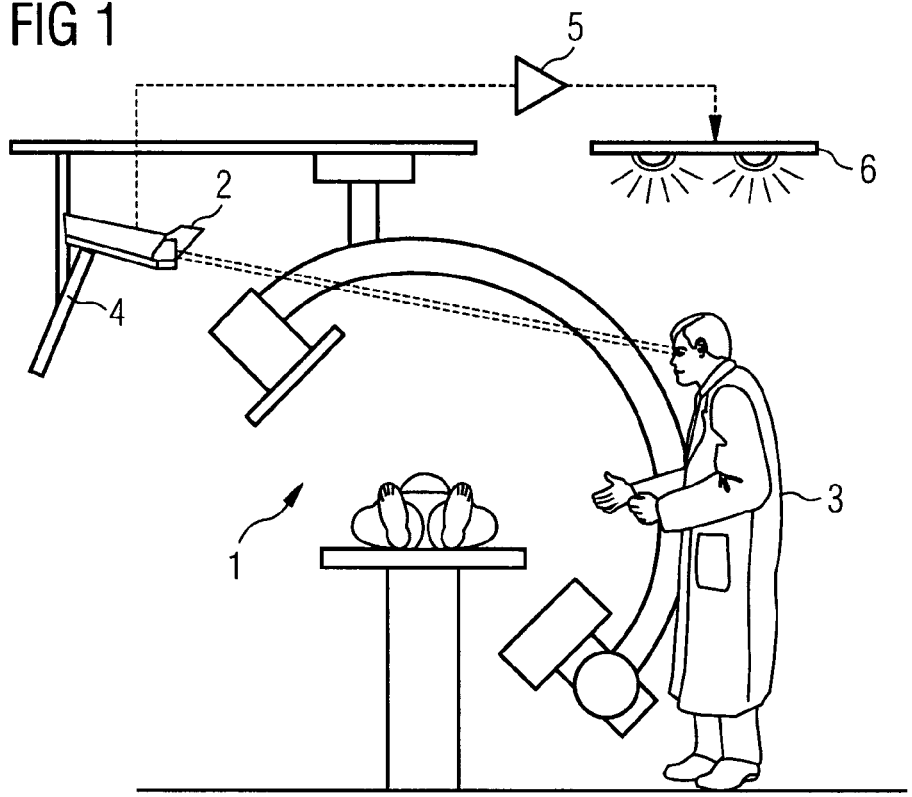
FIG. 1 shows, in accordance with a first exemplary embodiment, a C-arm x-ray system having at least one integrated camera, which observes the eye movement of the operator.

FIG. 1 shows, in accordance with a first exemplary embodiment, an x-ray system (C-arm system) 1 having at least one integrated camera 2, which observes the eye movement of the operator 3. As soon as the operator 3 looks at the monitor 4, the room light 6 is dimmed slightly. This takes place by way of a controller 5, which establishes a connection between camera 2 and room light 6. If the operator 3 does not look at the monitor 4, the room lighting level is brought up slightly again. The room lighting is not completely dimmed in order to enable the eye to adapt quickly. Excessively strong light/dark contrasts would be perceived as unpleasant as the eye is unable to adjust so quickly to extreme light/dark changes.

Figure 2:
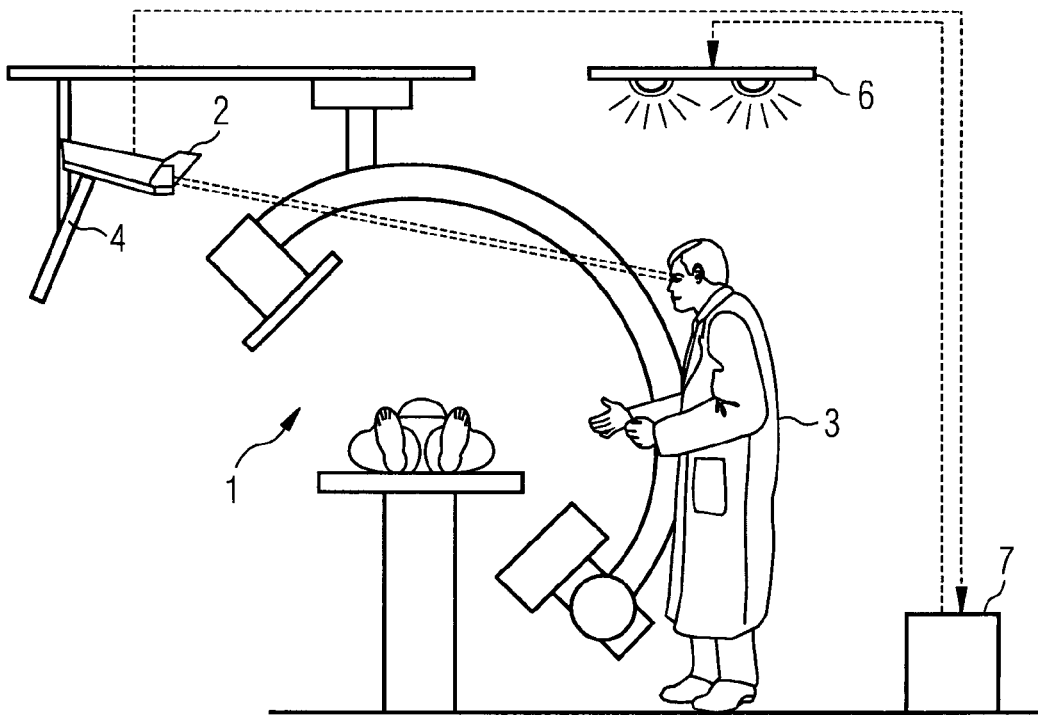
FIG. 2 shows, in accordance with a second exemplary embodiment, a C-arm x-ray system having at least one integrated camera, which observes the eye movement of the operator.

FIG. 2 shows, in accordance with a second exemplary embodiment, an x-ray system (C-arm system) 1 having at least one integrated camera 2, which observes the eye movement of the operator 3. Instead of a direct connection between camera 2 and light source 6 in the examination room, as is the case with the first exemplary embodiment, the controller is operated by way of a control device 7 of the x-ray system 1. This is advantageous in that further parameters or conditions related to the examination can be fed into the controller. By way of example, it could be advantageous to initiate dimming only during a fluoro run, e.g. while a catheter is being repositioned, since due to the relatively low dose used here, a contrast improvement is particularly expedient. The controller would thus still receive the quality of the currently displayed image as an input.

Furthermore, the degree of dimming can also be modulated as a function of the type of scene displayed or as a function of the individual image. The dimming is controlled according to the diagnostic content of the images.

The at least one camera 2 is preferably installed on a monitor gantry (not shown), since the visual field from the operator 3 to the monitor gantry is free. Other expedient positions can however also be selected, such as for instance the ceiling of the operating room.

The present invention is not restricted to the embodiments shown, but instead likewise comprises changes from the scope of the invention, this being defined by the appended claims.

The invention claimed is:

1. A method for optimizing an image display on an imaging apparatus of a medical system during a medical procedure, comprising:
    monitoring whether an operator of the medical system is looking at the imaging apparatus; and
    dimming a lighting in a room of the medical system if the operator is looking at the imaging apparatus for optimizing the image display on the imaging apparatus,
    wherein a camera monitors an eye of the operator to determine whether the operator of the medical system is looking at the imaging apparatus.

2. The method as claimed in claim 1, wherein the imaging apparatus is a monitor.

3. The method as claimed in claim 1, wherein the imaging apparatus is a video projector.

4. The method as claimed in claim 1, wherein a light source is attached to a head of the operator and a light receiver is arranged on the imaging apparatus for monitoring whether the operator is looking at the imaging apparatus.

5. The method as claimed in claim 1, wherein the medical system is an x-ray system.

6. The method as claimed in claim 1, wherein the dimming is controlled according to a diagnostic content of the image display.

7. The method as claimed in claim 5, wherein the imaging apparatus displays an image which is logged by the x-ray system.

8. A method for optimizing an image display on an imaging apparatus of a medical system during a medical procedure, comprising:
    monitoring whether an operator of the medical system is looking at the imaging apparatus; and
    increasing a contrast of the imaging apparatus if the operator is looking at the imaging apparatus for optimizing the image display on the imaging apparatus,
    wherein a camera monitors an eye of the operator to determine whether the operator of the medical system is looking at the imaging apparatus.

9. The method as claimed in claim 8, wherein a light source is attached to a head of the operator and a light receiver is arranged on the imaging apparatus for monitoring whether the operator is looking at the imaging apparatus.

10. A device for optimizing an image display on an imaging apparatus of a medical system during a medical procedure, comprising:
    a monitoring device that monitors whether an operator of the medical system is looking at the imaging apparatus; and
    a controller that optimizes the image display on the imaging apparatus if the operator is looking at the imaging apparatus,
    wherein the monitoring device is a camera that monitors an eye of the operator to determine whether the operator of the medical system is looking at the imaging apparatus.

11. The device as claimed in claim 10, wherein the controller optimizes the image display on the imaging apparatus by dimming a lighting in a room of the medical system.

12. The device as claimed in claim 10, wherein the controller optimizes the image display on the imaging apparatus by increasing a contrast of the imaging apparatus.

13. The device as claimed in claim 10, wherein the imaging apparatus is a monitor.

14. The device as claimed in claim 10, wherein the imaging apparatus is a video projector.

15. The device as claimed in claim 10, wherein the monitoring device comprises a light source attached to a head of the operator and a light receiver arranged on the imaging apparatus.

16. The device as claimed in claim 10, wherein the controller is integrated into a control device of the medical system.

17. The device as claimed in claim 10, wherein the medical system is an x-ray system.

18. The device as claimed in claim 17, wherein the imaging apparatus displays an image which is logged by the x-ray system.

* * * * *